US006650945B2

United States Patent
Helland et al.

(10) Patent No.: US 6,650,945 B2
(45) Date of Patent: Nov. 18, 2003

(54) IMPLANTABLE CARDIAC CORONARY SINUS LEAD HAVING A DEFIBRILLATION ELECTRODE OF SPLIT CONFIGURATION AND METHOD OF MANUFACTURE

(75) Inventors: John R. Helland, Saugus, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 112 days.

(21) Appl. No.: 09/771,388

(22) Filed: Jan. 26, 2001

(65) Prior Publication Data

US 2002/0103523 A1 Aug. 1, 2002

(51) Int. Cl.[7] .................................................. A61B 1/22
(52) U.S. Cl. ...................................... 607/122; 607/123
(58) Field of Search ............................ 607/4, 5, 9, 119, 607/122, 123

(56) References Cited

U.S. PATENT DOCUMENTS

| 4,969,463 | A | * | 11/1990 | Dahl et al. | |
| 5,174,288 | A | * | 12/1992 | Bardy et al. | 128/419 |
| 5,456,706 | A | * | 10/1995 | Pless et al. | |
| 5,800,465 | A | * | 9/1998 | Thompson et al. | 607/9 |
| 5,853,426 | A | | 12/1998 | Shieh | 607/5 |
| 5,919,222 | A | | 7/1999 | Hjelle et al. | 607/122 |
| 5,931,857 | A | | 8/1999 | Prieve et al. | 607/14 |
| 5,957,967 | A | | 9/1999 | Laske | 607/125 |
| 6,006,131 | A | | 12/1999 | Cooper et al. | 607/5 |
| 6,256,541 | B1 | * | 7/2001 | Heil et al. | |
| 6,430,449 | B1 | * | 8/2002 | Hsu et al. | 607/126 |

* cited by examiner

Primary Examiner—Mark Bockelman

(57) ABSTRACT

A chronic implantable cardiac lead for use in the coronary sinus region of the heart is described. The lead includes an elongated lead body having a distal end and a proximal end, a plurality of terminals at the proximal end of the lead body, and an electrode assembly including a plurality of electrodes at the distal end of the lead body. The electrode assembly includes at least one pacing electrode proximally spaced from the distal end and at least one defibrillation electrode including a first portion proximal to the pacing electrode and a second portion distal to the pacing electrode. A plurality of conductors connect each electrode to a respective given one of the terminals.

23 Claims, 3 Drawing Sheets

IMPLANTABLE CARDIAC CORONARY SINUS LEAD HAVING A DEFIBRILLATION ELECTRODE OF SPLIT CONFIGURATION AND METHOD OF MANUFACTURE

FIELD OF THE INVENTION

The present invention generally relates to an implantable cardiac lead for use with an implantable cardiac stimulation device. The present invention more particularly relates to such a lead adapted for use in the coronary sinus region of a heart and which employs a defibrillation electrode having a split configuration.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, and cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

When the ventricles of the heart are in need of defibrillation electrical therapy, it is desirable to deliver the defibrillation shock across as much of the ventricular myocardium as possible. If the defibrillation electrode combination includes either the case electrode or a superior vena cava defibrillation electrode, as is often practiced for the right heart, the defibrillation electrode for the left heart should have its distal end as near to the apex of the left ventricle as possible. In this example, this would then optimally position the defibrillation electrical field between the most myocardial tissue from the right heart to the left heart.

To maximize the usefulness of cardiac leads for implant in the coronary sinus region, the leads have included a pacing electrode to support left heart pacing for congestive heart failure. Since defibrillation electrodes are elongated as compared to pacing electrodes, the left ventricular pacing electrode has been located at the distal tip end of the lead, placing the left ventricular pacing electrode near to the left ventricular apex. While this is not an optimum pacing electrode placement, it has been found to be a more effective placement than a left ventricular pacing electrode placement proximal to the defibrillation electrode which, owing to the substantial link of the defibrillation electrode, would otherwise place the pacing electrode far up from the heart apex. An optimum left ventricular electrode placement would be between these extremes. As a result, it has been required that the defibrillation electrode extend from a point spaced from and proximal to the pacing electrode at the distal tip end. Hence, coronary sinus lead electrode placement has been a compromise, placing both the defibrillation electrode and pacing electrode in less than optimal locations for defibrillation and pacing when the lead is implanted in the coronary sinus region.

Leads for implant in the coronary sinus region may also provide left atrial therapy either alone or in addition to left ventricular therapy. These leads also include a left atrial pacing electrode and a left atrial defibrillation electrode.

SUMMARY OF THE INVENTION

The invention provides a chronic implantable cardiac lead for use in the coronary sinus region of a heart. The lead includes an elongated lead body having a distal end and a proximal end, a plurality of terminals at the proximal end of the lead body, an electrode assembly including a plurality of electrodes at the distal end of the lead body, and a plurality of conductors connecting each electrode to a respective given one of the terminals. The electrode assembly includes a pacing electrode proximally spaced from the distal end and a defibrillation electrode distal to the pacing electrode.

The present invention further provides an implantable cardiac lead for use in the coronary sinus region of the heart which locates both a defibrillation electrode for delivering a more optimal defibrillation electrical field for defibrillation and at least one pacing electrode for more optimal pacing. For ventricular defibrillation therapy, the lead includes an elongated defibrillation electrode which is split into first and second portions. The second portion extends to the distal tip of the lead to locate the defibrillation electrode for optimum defibrillation effectiveness near the left ventricular apex. At least one pacing electrode is positioned between the defibrillation electrode portions, placing the pacing electrode(s) to achieve effective pacing therapy in the middle of the left ventricle. The first portion of the defibrillation electrode is proximal to the pacing electrode so that it is positioned to cover the left ventricular base. Hence, both ventricular defibrillation and pacing therapy are rendered more optimally effective by the lead of the present invention.

The defibrillation electrode may, in accordance with one aspect of the present invention, be a coil electrode wherein the electrode portions are spaced apart electrical coils. Alternatively, in accordance with a further aspect of the present invention, the defibrillation electrode may be a plurality of ring electrodes with each electrode portion including a group of ring electrodes. At least one pacing electrode is then provided between the ring electrode groups.

The same lead configuration may also be employed for atrial therapy. Such an atrial lead would not have the length of a ventricular lead but the electrode configuration may be the same as described above.

Further, the present invention may be practiced to provide both atrial and ventricle therapy. Here, two electrode assemblies are provided on the lead, one for atrial pacing and defibrillation and the other for ventricular pacing and defibrillation. Each electrode assembly may include a defibrillation electrode split into spaced apart portions with at least one pacing electrode disposed in between the defibrillation electrode portions. The most distal ventricular defibrillation electrode portion preferably extends to or nearly to the distal tip end of the lead.

The lead, whether providing single chamber or dual chamber therapy, also preferably includes a plurality of connection terminals at its proximal end and a plurality of conductors for connecting each electrode with a respective different terminal. This permits the electrodes to be coupled to an implantable cardiac stimulation device configured to generate the required therapy to be applied by the electrodes.

The present invention still further provides an implantable cardiac stimulation system for use in stimulating a heart from the coronary sinus region of the heart. The system includes an implantable device that provides cardiac defibrillating energy, a lead having a distal end and a proximal end and an electrode assembly at the distal end of the lead. The electrode assembly includes a pacing electrode and a defibrillation electrode distal to the pacing electrode. The pacing and defibrillation electrodes may be coupled together when the device provides the defibrillating energy.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
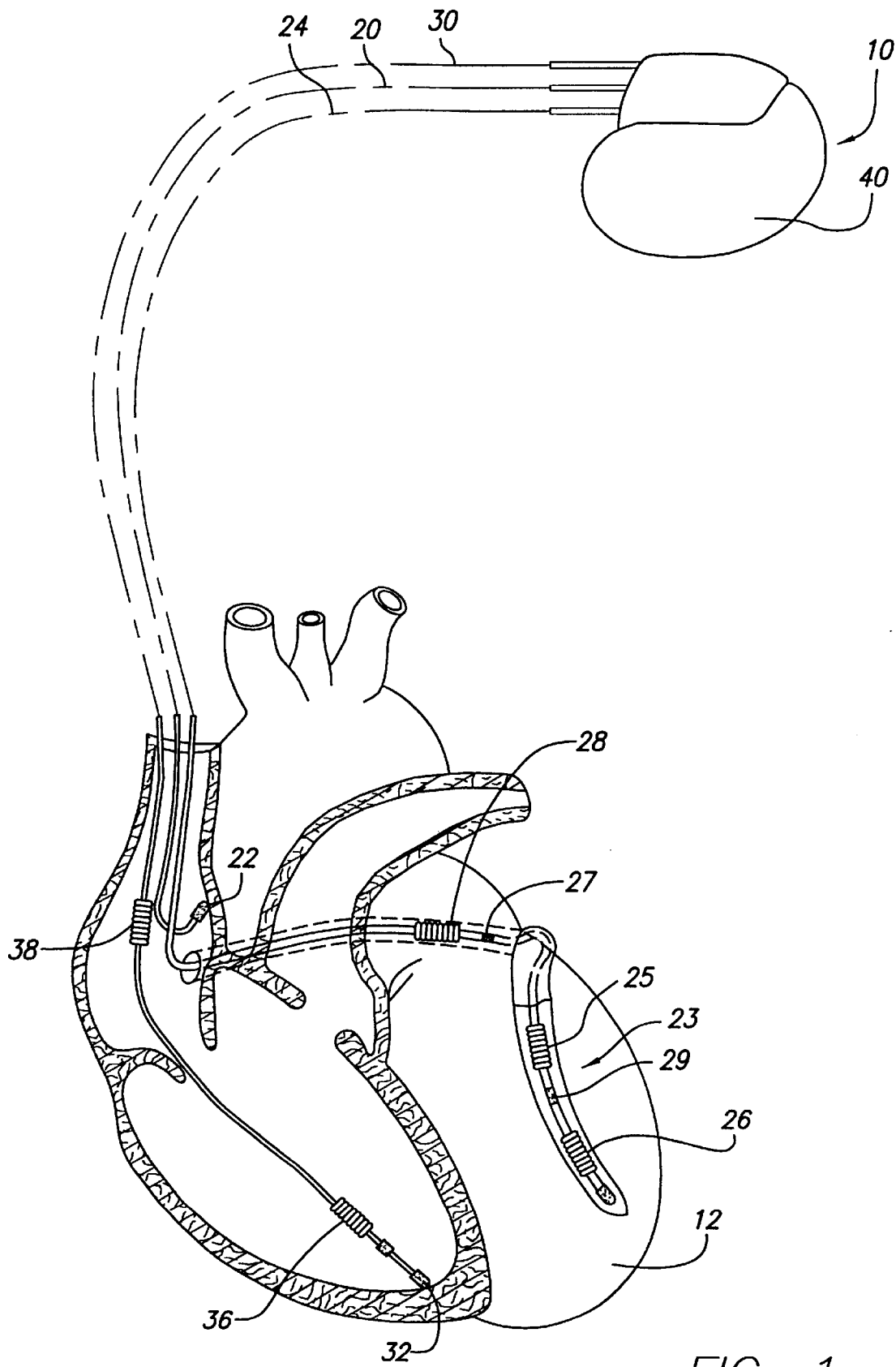
FIG. 1 is a simplified diagram illustrating an implantable cardiac stimulation device in electrical communication with a patient's heart by a lead system employing a coronary sinus region lead embodying the present invention.

As shown in FIG. 1, there is a stimulation device 10 in electrical communication with a patient's heart 12 by way of three leads, 20, 24, and 30 suitable for delivering multi-chamber stimulation and shock therapy. Lead 24 is a coronary sinus region lead embodying the present invention.

Lead 20 is a right atrial lead having at least an atrial tip electrode 22 which is typically implanted in the patient's right atrial appendage. The lead 20 permits the device to sense cardiac signals in the right atrium and to deliver right atrial chamber pacing stimulation therapy.

The stimulation device 10 is also shown in electrical communication with the patient's heart 12 by way of an implantable right ventricular lead 30 having, in this embodiment, a right ventricular tip electrode 32, a right ventricular coil electrode 36, and a superior vena cava coil electrode 38. Typically, the right ventricular lead 30 is transvenously inserted into the heart 12 so as to place the right ventricular tip electrode 32 in the right ventricular apex so that the right ventricular coil electrode will be positioned in the right ventricle and the superior vena cava coil electrode 38 will be positioned within the right atrium or the superior vena cava. Accordingly, the right ventricular lead 30 is capable of receiving cardiac signals, and delivering stimulation in the form of pacing and shock therapy to the right ventricle.

Lead 24 provides both left atrial therapy and, in accordance with the present invention through an electrode assembly 23, left ventricular pacing and defibrillation therapy. The lead 24 is elongated and designed for placement in the "coronary sinus region" of the heart through the coronary sinus ostiun and to extend adjacent to the left atrium and the left ventricle. As used herein, the phase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

As will be noted in FIG. 1, the lead distal end includes an electrode assembly 23 embodying the present invention. The electrode assembly 23 includes a defibrillation electrode including a first portion 25 and a second portion 26. In between the first and second defibrillation electrode portions 25 and 26 is a pacing electrode 29. The defibrillation electrode portion 26 extends from a point distal to the pacing electrode to the distal tip or adjacent to the distal tip end of the lead. In accordance with this embodiment, the defibrillation electrode is a coil electrode wherein the defibrillation electrode portions 25 and 26 are formed of coiled wire. The electrode portions 25 and 26 are electrically coupled together and are electrically isolated from the at least one pacing electrode 29.

The at least one pacing electrode 29 supports both sensing of cardiac activity of the heart and the delivery of pacing stimulation pulses to the left ventricle. The defibrillation electrode provides delivery of defibrillation stimulation pulses through the left ventricle. Because electrode portion 26 extends to the distal end or adjacent to the distal end or adjacent to the distal end of the lead 24, the defibrillation electrode will provide maximum defibrillation field strength through the ventricular myocardium when used, for example, in conjunction with the superior vena cava coil electrode 38, and/or the right ventricular defibrillation electrode 36. Also, since the at least one pacing electrode is displaced from the distal tip end of the lead 24 by only a fraction of the overall length of the defibrillation electrode, it will provide effective left ventricular pacing and sensing as well.

To complete the description of the lead 24, the lead 24 further includes at least one left atrial pacing electrode 27 and a left atrial defibrillation coil electrode 28. The electrode 27 provides both sensing of atrial activity of the heart and delivery of pacing stimulation pulses to the left atrium. The defibrillation coil electrode 28 permits atrial defibrillation stimulation pulses to be delivered to the left atrium. Alternatively, the defibrillation electrode 28 and pacing electrode 27 may be configured as electrode assembly 23 as will be seen subsequently. Also, as will be seen subsequently, lead 24 may be modified by eliminating the atrial electrodes 27 and 28 and/or the electrode portion 25 without departing from the present invention.

Figure 2:
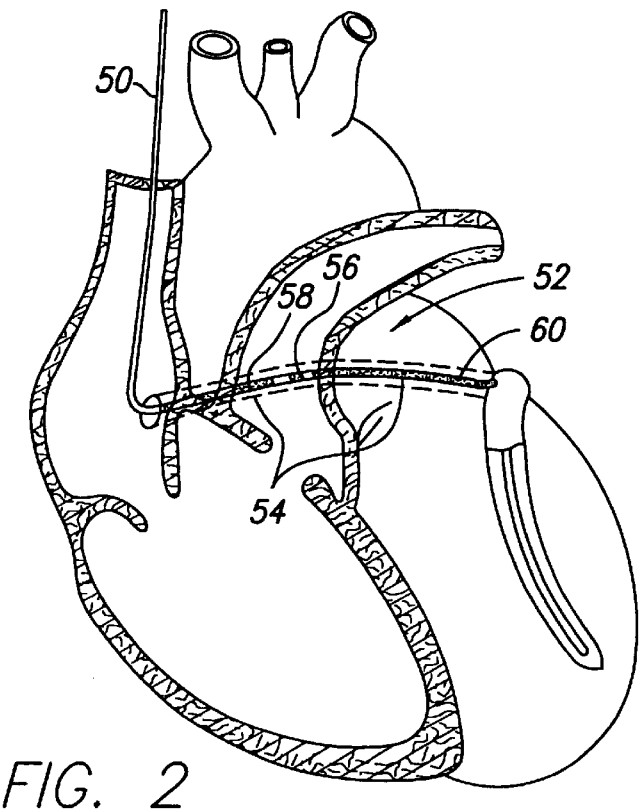
FIG. 2 is a simplified diagram of a human heart illustrating a coronary sinus region lead embodying the present invention for use in delivering atrial therapy to the heart.

FIG. 2 shows another coronary sinus region lead 50 embodying the present invention. The lead 50 is configured to deliver pacing stimulation pulses to the left atrium, sense atrial activity, and deliver defibrillation stimulation pulses to the left atrium. To that end, the lead 50 includes an electrode assembly 52 at the distal end of the lead including a defibrillation electrode 54 and at least one pacing electrode 56. The defibrillation electrode 54, in accordance with this embodiment, is a coil electrode comprising a first coil electrode portion 58 and a second coil electrode portion 60. The electrode portion 60 extends from a point distal to the pacing electrode 56 to the distal tip, or adjacent to the distal tip end of the lead. As in the previous embodiment, the defibrillation electrode portions 58 and 60 are electrically coupled together and electrically isolated from the at least one pacing electrode 56.

Figure 3:
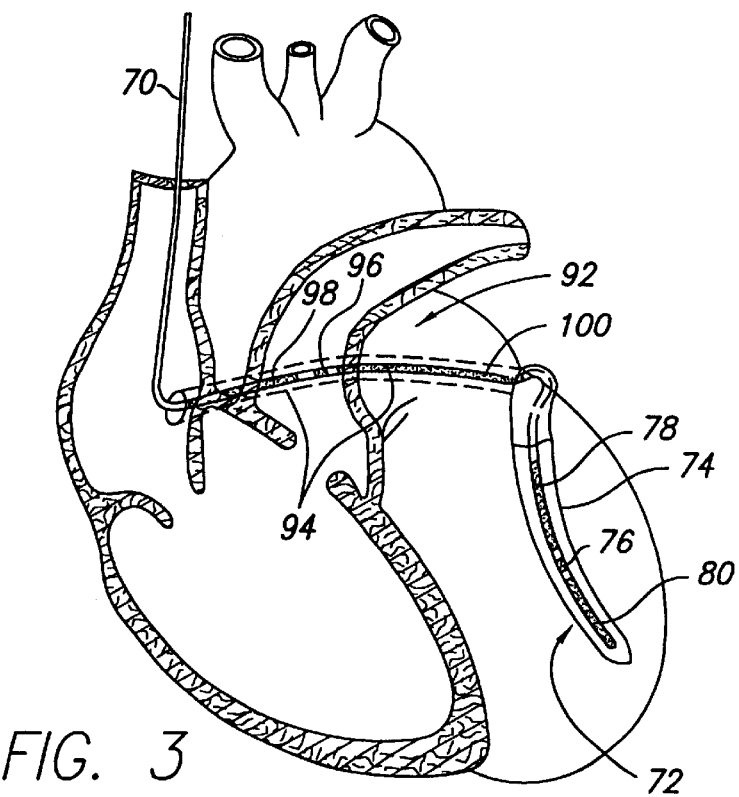
FIG. 3 is a simplified diagram of a human heart illustrating a coronary sinus region lead embodying the present invention for use in delivering either atrial or ventricular therapy to the heart.

FIG. 3 shows another coronary sinus region lead 70 embodying the present invention. The lead 70 is configured to provide both atrial therapy and ventricular therapy. More specifically, the lead 70 is configured to deliver pacing stimulation pulses to the left atrium, sense atrial activity, deliver defibrillation stimulation pulses to the left atrium, deliver pacing stimulation pulses to the left ventricle, sense ventricular activity, and deliver defibrillation stimulation pulses to the left ventricle. To that end, the lead 70 includes a first electrode assembly 72 at the distal end of the lead 70 and a second electrode assembly 92 proximal to the first electrode assembly 72. The first electrode assembly 72 includes a ventricular defibrillation electrode 74 and a ventricular pacing electrode 76. The defibrillation electrode 74, in accordance with this embodiment, is a coil electrode comprising a first coil electrode portion 78 and a second coil electrode portion 80. The electrode portion 80 extends from a point distal to the pacing electrode 76 to the distal tip or adjacent to the distal tip of the lead. As in the previous embodiments, the defibrillation electrode portions 78 and 80 are electrically coupled together and electrically isolated from the pacing electrode 76.

The second electrode assembly 92 includes an atrial defibrillation electrode 94 and an atrial pacing electrode 96. The defibrillation electrode 94, in accordance with this embodiment, also is a coil electrode comprising a first coil electrode portion 98 and a second coil electrode portion 100. The electrode coil portions 98 and 100 are electrically coupled together and electrically isolated from the pacing electrode 96.

The electrode assemblies 72 and 92 are spaced apart for maximum effectiveness. To that end, electrode assembly 92 is spaced from electrode assembly 72 so that when electrode assembly 72 is adjacent the left ventricle within the coronary sinus region, the electrode assembly 92 is adjacent the left atrium within the coronary sinus region.

Figure 4:
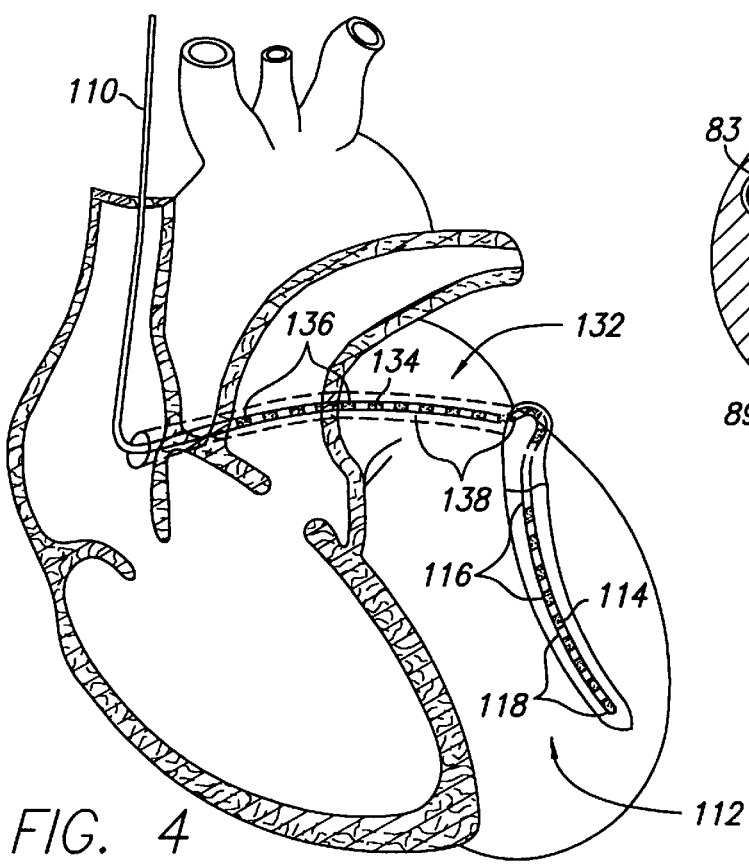
FIG. 4 is a simplified diagram of a human heart illustrating another coronary sinus region lead embodying the present invention for use in delivering either atrial or ventricular therapy to the heart.

FIG. 4 shows still another coronary sinus region lead 110 embodying the present invention. The lead 110, like lead 70 of FIG. 3 is configured to deliver pacing stimulation pulses to the left atrium, sense atrial activity, deliver defibrillation stimulation pulses to the left atrium, deliver pacing stimulation pulses to the left ventricle, sense ventricular activity, and deliver defibrillation stimulation pulses to the left ventricle. To provide such functionality, the lead 110 includes a left ventricular electrode assembly 112 and a left atrial electrode assembly 132. The ventricular electrode assembly 112 is positioned at the distal end of the lead 110 and includes a ventricular pacing electrode 114 and a ventricular defibrillation electrode comprising a first portion formed by a first group 116 of ring electrodes and a second portion formed by a second group 118 of ring electrodes. The ring electrodes of the defibrillation electrode are electrically coupled together but electrically isolated from the pacing electrode 114. Again, the second portion or group of ring electrodes 118 extends from a point distal to the pacing electrode 114 to the distal tip or adjacent to the distal tip of the lead 110.

Similarly, the atrial electrode assembly includes an atrial pacing electrode 134 and an atrial defibrillation electrode comprising a first portion formed by a first group 136 of ring electrodes and a second portion formed by a second group 138 of ring electrodes. Again, the defibrillation electrode ring electrodes are electrically coupled together but electrically isolated from the pacing electrode 134.

The electrode assemblies 112 and 132 are spaced apart for maximum effectiveness. To that end, electrode assembly 132 is spaced from electrode assembly 112 so that when electrode assembly 112 is adjacent the left ventricle within the coronary sinus region, the electrode assembly 132 is adjacent the left atrium within the coronary sinus region.

Figure 6:
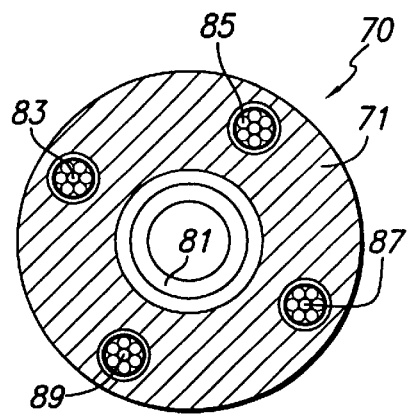
FIG. 6 is a cross-sectional view taken along lines 6—6 of FIG. 5.
Figure 5:
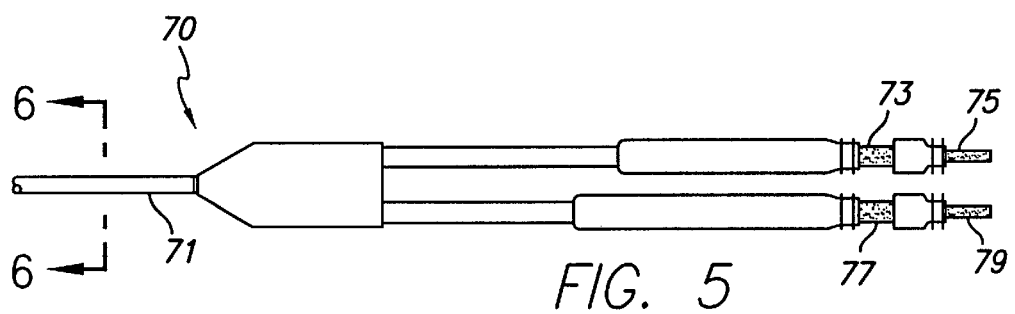
FIG. 5 is a side plan view, to an enlarged scale, of the proximal end of the lead of FIG. 3.

FIGS. 5 and 6 show the proximal end of the lead 70 of FIG. 3. The lead 70 includes an elongated lead body 71 which includes at its proximal end a plurality of terminals 73, 75, 77, and 79. The lead body further includes a plurality of lumen conductors 83, 85, 87, and 89 and a conductive stylet bearing coil 81. The lumen conductors and stylet coil electrically connect each terminal to a respective different lead electrode. For example, terminal 73 may be connected to the left atrial pacing electrode 96 by conductor 83, terminal 75 may be connected to the left atrial defibrillation electrode 94 by conductor 85, terminal 77 may be connected to the left ventricular pacing electrode 76 by stylet coil 81, and terminal 79 may be coupled to the left ventricular defibrillation electrode 74 by the parallel combination of conductors 87 and 89. Conductors 87 and 89 may be advantageously coupled in parallel because of the higher currents required for ventricular defibrillation.

In accordance with the embodiments previously described, the defibrillation electrodes may have an overall length of between 3 cm and 12 cm. The defibrillation electrode portions may be of equal length or different lengths. The pacing electrode may have, for example, a 1 mm length. As a specific example, each defibrillation electrode portion may have a length of 1.5 cm while being spaced 1.5 cm. With respect to those embodiments wherein the defibrillation electrodes are formed of groups of ring electrodes, each ring electrode may have a length of 1 mm, for example, with 1 mm spacing.

Figure 7:
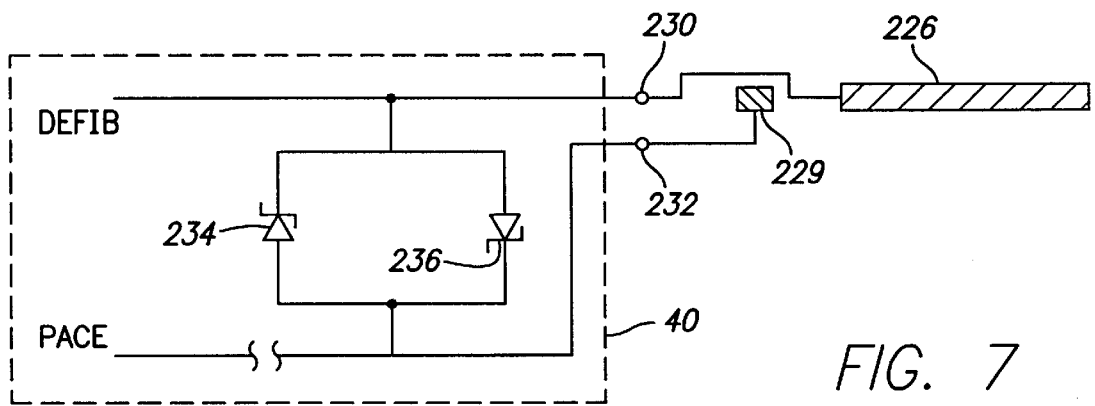
FIG. 7 is a simplified schematic diagram illustrating further aspects of the present invention.

FIG. 7 is a schematic diagram of a system 200 embodying the present invention. Here, the distal defibrillation electrode 226 and the proximal pacing electrode 229 are shown coupled to output terminals 230 and 232 of the device 40. A pair of zener diodes 234 and 236 are arranged to isolate the pacing electrode 229 from the defibrillation electrode 226 when a pacing voltage is applied to terminal 232 and to couple the electrodes 226 and 229 together when a comparatively high voltage defibrillation voltage is applied to terminal 230. Alternatively, the electrodes 226 and 229 may be selectively coupled together by switches within the device 40 in a manner known in the art.

As thus can be seen from the foregoing, the present invention provides a coronary sinus region implantable lead which provides both effective pacing therapy and defibrillation therapy. Both the defibrillation electrode and the pacing electrode are positioned adjacent myocardial tissue of the heart to provide efficient pacing and defibrillation therapy. The foregoing is accomplished by splitting the defibrillation electrode into electrically connected portions and locating the pacing electrode in between the split defibrillation electrode portions. This allows for defibrillation shock electrical fields to be located more appropriately from the distal tip of the lead to the proximal edge of the proximal portion of the defibrillation electrode to allow a better dispersion of the electrical shock field. At the same time, the pacing electrode is in an appropriate location for effective pacing stimulation.

While the invention has been described by means of specific embodiments and applications thereof, it is understood that numerous modifications and variations could be made thereto by those skilled in the art without departing from the spirit and scope of the invention. It is therefore to be understood that within the scope of the claims the invention may be practices otherwise than as specifically described herein.

What is claimed is:

1. A chronic implantable cardiac lead for use in the coronary sinus region of a heart, the lead comprising:
    an elongated lead body having a distal end and a proximal end;
    a plurality of terminals at the proximal end of the lead body;
    an electrode assembly including a plurality of electrodes at the distal end of the lead body; and
    a plurality of conductors connecting each electrode to a respective given one of the terminals,
    the electrode assembly including at least one left ventricular pacing electrode proximally spaced from the distal end and at least one left ventricular defibrillation electrode including a first portion proximal to the pacing electrode and a second portion distal to the pacing electrode, the first portion electrically coupled directly to the second portion within the lead by the plurality of conductors.

2. The cardiac lead of claim 1 wherein the left ventricular defibrillation electrode is a coil electrode and wherein the first and second portions each comprise an electrical coil.

3. The cardiac lead of claim 1 wherein the first and second defibrillation electrode portions comprise a first and second respective group of ring electrodes.

4. The cardiac lead of claim 1 wherein the second portion of the left ventricular defibrillation electrode extends distally to the distal end or adjacent to the distal end.

5. The cardiac lead of claim 1 further comprising an additional electrode assembly having a left atrial pacing electrode proximally spaced from the distal end and a left atrial defibrillation electrode having a first portion proximal to the left atrial pacing electrode and a second portion distal to the left atrial pacing electrode.

6. The cardiac lead of claim 1 wherein the first defibrillation electrode portion and the second defibrillation electrode portion are ring electrodes.

7. The cardiac lead of claim 1 the first and second portion of the left ventricular defibrillation electrode are electrically isolated from the left ventricular pacing electrode.

8. A chronic implantable cardiac lead for use in the coronary sinus region of a heart, the lead comprising:
    an elongated lead body having a distal end and a proximal end;
    a plurality of terminals at the proximal end of the lead body;
    a first electrode assembly at the distal end of the lead body;
    a second electrode assembly proximal to the first electrode assembly;
    the first electrode assembly having a left ventricular pacing electrode and a left ventricular defibrillation electrode, the left ventricular defibrillation electrode having a first portion proximal to the left ventricular pacing electrode and a second portion distal to the left ventricular pacing electrode;
    the second electrode assembly having a left atrial pacing electrode and a left atrial defibrillation electrode, the left atrial defibrillation electrode having a first portion proximal to the left atrial pacing electrode and a second portion distal to the left atrial pacing electrode; and
    a plurality of conductors connecting the electrodes with the terminals, the first portion of the left ventricular defibrillation electrode electrically coupled within the lead directly to the second portion of the left ventricular defibrillation electrode, and the first portion of the left atrial defibrillation electrode electrically coupled within the lead directly to the second portion of the left atrial defibrillation electrode.

9. The cardiac lead of claim 8 wherein the second electrode assembly is spaced from the first electrode assembly so that with the first electrode assembly being closely adjacent the left ventricle within the coronary sinus region, the second electrode assembly is closely adjacent the left atrium within the coronary sinus region.

10. The cardiac lead of claim 8 wherein at least one of the left ventricular defibrillation electrode and the left atrial defibrillation electrode is a coil electrode with the first and second portions being electrical coils.

11. The cardiac lead of claim 8 wherein the first portion and the second portion of the defibrillation electrode of at least one of the first and second electrode assemblies comprise a first and second respective group of ring electrodes.

12. The cardiac lead of claim 8 wherein the second portion of the left ventricular defibrillation electrode of the first electrode assembly extends distally to the distal end or adjacent to the distal end.

13. The cardiac lead of claim 8 wherein the electrode assembly is spaced from the additional electrode assembly so that the electrode assembly is adjacent the left ventricle within the coronary sinus region and the additional electrode assembly is closely adjacent the left atrium within the coronary sinus region.

14. A chronic implantable cardiac lead for use in the coronary sinus region of a heart, the lead comprising:

an elongated lead body having a distal end and a proximal end;

a plurality of terminals at the proximal end of the lead body;

an electrode assembly including a plurality of electrodes at the distal end of the lead body; and a plurality of conductors connecting each electrode to a respective given one of the terminals, the electrode assembly including a left ventricular pacing electrode proximally spaced from the distal end and a left ventricular defibrillation electrode having a first portion proximal to the left ventricular pacing electrode and a second portion distal to the left ventricular pacing electrode, the first portion electrically coupled directly to the second portion within the lead.

15. The cardiac lead of claim 14 wherein the left ventricular defibrillation electrode is a coil electrode.

16. The cardiac lead of claim 14 wherein the left ventricular defibrillation electrode extends distally to the distal end.

17. The cardiac lead of claim 14 wherein the first and second portion of the left ventricular defibrillation electrode are electrically isolated from the left ventricular pacing electrode.

18. A chronic implantable cardiac lead for use in the coronary sinus region of a heart, the lead comprising:

a lead body having a distal end and a proximal end; and an electrode assembly comprising:

a pacing electrode proximally spaced from the distal end of the lead body; and a defibrillation electrode split into a first portion and a second portion, the pacing electrode disposed between the first portion and the second, the first portion and the second portion electrically coupled directly within the lead, and the first portion and the second portion electrically isolated from the pacing electrode.

19. The cardiac lead of claim 18 further comprising:

a plurality of terminals at the proximal end of the lead body; and a plurality of conductors coupling the pacing electrode and the defibrillation electrode to a respective given one of the terminals.

20. The cardiac lead of claim 19 further comprising:

an additional electrode assembly having a left atrial pacing electrode proximally spaced from the distal end and a left atrial defibrillation electrode split into a first portion proximal to the left atrial pacing electrode and a second portion distal to the left atrial pacing electrode, the first portion of the left atrial defibrillation electrode electrically coupled to the second portion of the left atrial defibrillation electrode, and the first and second portion of the left atrial defibrillation electrode electrically isolated from the left atrial pacing electrode;

wherein the pacing electrode of the electrode assembly is a left ventricular pacing electrode and the defibrillation electrode of the electrode assembly is a left ventricular defibrillation electrode.

21. The cardiac lead of claim 20 wherein the left atrial defibrillation electrode is a coil electrode.

22. The cardiac lead of claim 20 wherein the left atrial pacing electrode supports both sensing of cardiac activity of the heart and the delivery of pacing stimulation pulses to the left atrial.

23. The cardiac lead of claim 22 wherein the left ventricular pacing electrode supports both sensing of cardiac activity of the heart and the delivery of pacing pulses to the left ventricle.

* * * * *